United States Patent [19]

Ebner et al.

[11] Patent Number: 4,626,412
[45] Date of Patent: Dec. 2, 1986

[54] METHOD AND APPARATUS FOR CARRYING OUT CATALYZED CHEMICAL REACTIONS AND FOR STUDYING CATALYSTS

[75] Inventors: Jerry R. Ebner; John T. Gleaves, both of St. Charles, Mo.

[73] Assignee: Monsanto Company, St. Louis, Mo.

[21] Appl. No.: 682,028

[22] Filed: Dec. 14, 1984

[51] Int. Cl.⁴ .......................................... G01N 31/10
[52] U.S. Cl. ...................................... 422/50; 436/37; 422/68; 422/78; 422/83
[58] Field of Search ....................... 422/50, 68, 83, 78; 436/37, 52, 173

[56] References Cited

U.S. PATENT DOCUMENTS 3,907,707  3/1973  Raffelson et al. .................. 252/260
3,992,109  11/1976 Bock ................................. 436/52 X
4,457,905  12/1982 Ebner ................................ 423/568

OTHER PUBLICATIONS

R. P. Merrill, *Cat. Rev.*, 4 (1), 115 (1970).
R. P. Palmer and J. N. Smith, *Cat. Rev. Sci. Eng.*, 12 (2), 279 (1975).
H. Saltsburg, *Ann. Rev. Phys. Chem.*, 24, 493 (1973).
Mark J. Cardillo, *Ann. Rev. Phys. Chem.*, 32, 331–357, (1981).
C. O. Bennett, *Catalysis Under Transient Conditions*, 1–32, ACS Symposium Series 178, ACS, Washington, D.C., (1982).
R. H. Jones, D. R. Olander, W. J. Sickhaus and J. A. Schwarz, *J. Vac. Sci. Technol.* 9(6), 1429 (1972).
D. R. Jenkins and M. A. Voisey, *J. of Phy.*, E6, 827 (1973).
Wade L. Fite, *Int. J. Mass Spec. and Ion Phy.*, 16, 109 (1975).
R. J. Madix and M. Boudart, *J. Catal.* 7, 240 (1967).
R. J. Madix and A. A. Susu, *Surf. Sci.*, 20, 377 (1970).
C. J. Machiels, *Catalysis Under Transient Conditions*, 239–251, ACS Symposium Series 178, ACS, Washington, D.C., (1982).
B. S. Balzhinimaev, V. E. Ponomarev, G. K. Boreskov, and A. A. Ivanov, *React. Kinet. Catal. Lett.*, 24 (3–4), 219–224, (1984).
A. Miyamoto, T. Ui, Y. Murakami, *J. of Catalysis*, 88, 526–529, (1984).
S. L. Bernasek and G. A. Somorjai, *J. Chem. Phys.*, 62, 3149 (1975).
J. N. Smith, Jr., R. L. Palmer, and D. A. Vroom, *J. Vac. Sci. Technol.*, 10, 373 (1973).
P. J. Hart and H. R. Friedli, *Chem. Comm.*, 11, 621 (1970).

*Primary Examiner*—Kenneth M. Schor
*Attorney, Agent, or Firm*—John H. Beusen; Thomas E. Kelley; Arthur E. Hoffman

[57] ABSTRACT

Disclosed are an apparatus and a method for carrying out and studying catalysis and catalyzed chemical reactions. Disclosed is a reactor with a catalyst zone, under vacuum, into which a very rapid pulse of reactant gas is pulsed. The products are analyzed by a real-time method of analysis, such as mass spectrometry. The apparatus and method can detect reaction intermediates and products, and can indicate their sequence of production.

1 Claim, 5 Drawing Figures

METHOD AND APPARATUS FOR CARRYING OUT CATALYZED CHEMICAL REACTIONS AND FOR STUDYING CATALYSTS

FIELD OF THE INVENTION

This invention relates to carrying out and studying of catalysis and catalyzed chemical reactions, particularly to heterogeneous catalysis.

BACKGROUND

Catalyzed chemical reactions are widely used and are commercially very important. As a result, the development of new catalysts and catalyzed processes has been the object of a significant amount of technical development. The development of new catalysts and catalyzed reactions has been hampered by the difficulty encountered in obtaining basic information about the physical and chemical processes involved in catalytic activity and catalytic reactions, such as reaction intermediates, reaction mechanisms, adsorption and desorption of reactants and products in catalytic reactions, oxidation and reduction of catalysts, catalyst poisons, the concentration of reactants on a catalyst surface, and others.

Classically, this kind of basic information about the chemical and physical processes of catalysis has been deduced primarily from analysis of the final products of the reaction. Conclusions have been based on final products because of the difficulty in isolating and analyzing reaction intermediates, many of which are highly fragile and reactive species. Being able to determine directly the identity of these intermediates and to follow their production and consumption during the reaction would increase the understanding of catalysis and would facilitate the development of catalysts and catalytic processes.

One method that has been used to study the interaction of catalytic surfaces with reactant molecules is called molecular beam mass spectrometry. In this technique, a stream of molecules of reactant gas (a molecular beam) is directed at a target of the catalytic material, with the target oriented at an angle to the molecular beam. The molecules of the reactant gas strike the target, some of them react to form products and intermediates, and they rebound off the target in the direction of an aperature. A portion of the rebounding molecules pass through the aperature into the ionization chamber of a mass spectrometer, which analyzes the mixture for reactants, intermediates, and products.

A variation on this molecular beam technique is called modulated molecular beam mass spectrometry, in which the initial molecular beam of reactant gas is modulated, such as with a rotating "chopper", to produce a series of pulses of the reactant gas. The result is that a series of pulses of gas enter the mass spectrometer for analysis.

In these molecular beam techniques, the entire assembly is enclosed and is operated in a vacuum. The vacuum is necessary to achieve the molecular flow to form the molecular beam, and is necessary for operation of the mass spectrometer.

The vacuum required, along with the fact that the molecules strike the catalyst target and rebound to the detector combine to make the number of reaction opportunities for each molecule of reactant very small. It has been estimated that the number of collisions between a given molecule of reactant gas and the target catalyst would be 10 or less, and that the number of collisions between a given molecule of reactant gas and other gas molecules would also be 10 or less. This means that these molecular beam techniques are practical only for highly reactive systems, in which sufficient reaction occurs in the small number of reaction opportunities to produce detectable amounts of products and intermediates. Most commercially important catalyzed reaction systems are not reactive enough for use with molecular beam techniques. The catalyst suitable for use with molecular beam techniques must be made into a target with a surface regular enough so that the direction of rebound of the reactant gas molecules can be directed toward the mass spectrometer. Not all catalysts can be formed into such a target.

Conventional techniques have been adapted to try to isolate and analyze for reaction intermediates. One common technique involves a reactor containing a catalyst, through which an inert carrier gas flows continuously. A pulse of reactant gas is injected into the carrier gas and is carried through the catalyst. As the product gas exits the reactor, samples are taken and analyzed. This type of system is normally operated at or near atmospheric pressure. The number of collisions between an average molecule of reactant gas and the catalyst is very high, and has been estimated to be far greater than $10^6$. Similarly, the number of oollisions between an averaqe moleoule of reactant qas and other gas moleoules has been estimated to be far greater than $10^5$. Due to the large number of reaction opportunities, the number of fragile and highly reactive intermediates that emerge from the catalyst is very small, and is usually too small to be detected.

The method and apparatus of this invention overcome some of the problems associated with prior art techniques to study catalysis. This invention preserves and detects fragile and highly reactive reaction intermediates of catalyzed chemical reactions, and preserves the time sequence of reactant/intermediate/product species evolved in a catalyzed chemical reaction.

SUMMALRY OF THE INVENTION

One embodiment of this invention is an apparatus comprising:
  a. an enclosed housing with a means for producing a substantial vacuum within said housing;
  b. within said housing, a reactor with a catalyst zone, adapted to pass a reactant gas through said catalyst zone to produce a product gas;
  c. a means to introduce a very rapid pulse of said reactant gas to said catalyst zone;
  d. an outlet means from said catalyst zone from which a pulse of product gas may exit said catalyst zone;
  e. within said housing, a means for resolving said pulse of product gas to produce a resolved pulse of product gas in which the molecules of product gas are moving in substantially parallel paths;
  f. a means for real time analysis of said resolved pulse of product gas; and
  g. a means for coordinating the actions of said rapid pulse means and said analysis means.

Another embodiment of this invention is a method, comprising:
  a. introducing a very rapid pulse of a reactant gas to a catalyst zone in an enclosure under a substantial vacuum.
  b. passing said reactant gas through said catalyst zone to produce a pulse of product gas;

c. resolving said pulse of product gas to produce a resolved pulse of product gas in which the molecules of the product gas pulse are moving in substantially parallel paths;

d. analyzing said resolved pulse of product gas in real time, and in coordination with said very rapid pulse of reactant gas.

The method of this invention will be referred to herein as temporal analysis of products, or TAP, and the apparatus will be referred to as a temporal analysis of products reaction system, or TAPRS.

DISCUSSION OF THE INVENTION

TAP can be used with any reactant gas, or any other reactant that will exist as a gas under the vacuum and temperature of the TAPRS. The reactant gas can either be a single component or have multiple components. The reactant gas may also be mixed with an inert diluent. However, an inert diluent is often not necessary, and may, in some instances, make analysis of the products and intermediates more difficult.

If the reactant gas has more than one component or if a diluent is used, it is preferable to mix the gases prior to introduction of the reactant pulse to the catalyst zone. This can be accomplished in a number of ways, such as mixing in the storage feed tank, or by inclusion of a mixing zone, either prior to the pulsing mechanism or between the pulsing mechanism and the catalyst zone. The mixing zone could be a simple tubular segment or it may be a cone with the wide end corresponding to the diameter of the reactor, and the narrow end to the opening in the pulsing mechanism. It could contain baffles, be packed with inert solid particles with low surface area, such as sintered silica, silicon carbide, stainless steel, pyrex, and the like, or have some other means of creating mixing turbulence.

The reactant feed system also includes a means for generating a very rapid pulse of reactants. As used herein the phrase "very rapid pulse of reactant gas" means a discrete brief injection of reactant gas preferably lasting no longer than 10 milliseconds, more preferably no longer than 1 milliseconds, and most preferably not more than 0.5 milliseconds, although in some circumstances the pulse may last somewhat longer than 10 milliseconds. It is very difficult using normal techniques to get a pulse shorter than 5 microseconds. The times for the pulses are measured at the full width at half the maximum of the pulse curve. The very rapid pulse of reactant gas can be generated in a number of ways, including, but not limited to a "chopper", e.g. a rotating disc with one or more segments removed, rotating in the stream of reactant gas, or more preferably, a high speed gas pulsing valve. High speed valves suitable for this use are available commercially. Suitable high speed valves include modified miniature solenoid valves, piezo electric valves, pulsed molecular beam valves, and any other valve that opens and closes sufficiently rapidly to produce a very rapid pulse of reactant gas.

The very rapid pulse of reactant gas could be a single pulse, or could be multiple pulses up to 500 pulses per second, and under some conditions even more pulses per second. It is preferred that the pressure of the reactant gas and the duration of the very rapid pulse be regulated so that each pulse contains $10^{10}$ to $10^{21}$ molecules per pulse, more preferably $10^{13}$–$10^{18}$ s molecules per pulse.

There may be some circumstances under which it would be desirable to pulse two reactant gases separately, either simultaneously or at different times. For instance if two gases react under ambient conditions it would be desirable to pulse them separately to avoid premature reaction. Also, if one component of a reactant gas mixture moves through the catalyst zone very quickly, but participates in a later step in a multistep reaction, it may no longer be present in the catalyst zone at the time it is required in the reaction. In this situation, it may be desirable to introduce a pulse of this particular component at a somewhat later time than the other components. In order to accomplish this kind of plural pulsing, a plurality of pulsing means may be required.

There may also be some circumstances in which a continuous feed may be desirable, along with either singular or plural pulsing. For example continuous feed of a component might be used to solve the problem discussed above, where the component has left the reactor prior to its being required in the reaction. Additionally, it may be desired to investigate how a catalyst performs if a substance is adsorbed on the catalyst surface. This can be accomplished by continuously feeding the adsorbing substance prior to and during pulsing of the reactant gas. Other situations in which a continuous feed would be desirable would be known to one skilled in the art. Continuous feeding is most conveniently accomplished using a low pressure capillary feed system or a leak valve. The rate of continuous feed should not be so great as to increase the pressure, in the catalyst zone or elsewhere in the enclosure, beyond operable limits.

In order to accommodate this multiplicity of feeds, it is preferred that the mixing zone be connected to the reactor and adapted for attachment of these feed lines.

The reactor can be of a variety of shapes, but preferably it is tubular in shape to hold the catalyst. The inlet end of the reactor is adapted to receive the very rapid pulse of reactant gas. This can normally be accomplished with a simple small tubular connection, or by direct connection to the mixing zone. It may be advantageous under some circumstances to include a baffle in the inlet to the reactor to avoid the presence of dead space. It is also preferred that the inlet be equipped with a means of retaining the catalyst in the reactor. However this retaining means must not unduly interfere with entry of the pulse of reactant gas. A screen is the preferred retaining means, more preferably a stainless steel screen.

The enclosure and reactor and its contents must be maintained under substantial vacuum during operation. As used herein, the phrase "substantial vacuum" means a background pressure no greater than $10^{-4}$ torr, preferably no greater than $10^{-6}$ torr Higher pressures within this range are more common when using a continuous feed, and intermittent pressures may be slightly higher during a pulse. In order to accomplish this, the reactor is in an enclosure fitted with a means for attaining a substantial vacuum, such as a vacuum pump, including but not limited to oil diffusion pumps, turbomolecular pumps, ion pumps, and cryo pumps. Cryogenic traps and cryogenic surfaces can be used to assist in maintaining vacuum.

It is preferred that the catalyzed reaction be run at controlled temperature, so it is desired that there be some means of controlling the temperature of the reactor. This can be done by use of a jacket or coils for a temperature control fluid or by resistance heating. The temperature control means should be able to provide for isothermal operation or for operation with a controlled rising or falling temperature. It is preferred that the reactor and the temperature control means be able to operate over a wide temperature range, for instance from about 100° K. to about 900° K., or that separate reactors and/or separate temperature control means be fashioned to operate at a desired temperature.

The reactor may be constructed of stainless steel, ceramic, or other suitable materials. The catalyst zone is usually simply a cavity in the reactor and can be of any convenient size. It is preferred that the catalyst zone be cylindrical, with a diameter from about 0.2 cm to about 2.5 cm and with a length from about 0.5 cm to about 5 cm, although it may be larger or smaller to fit the circumstances.

The catalyst may be particles packed into the catalyst zone or may be coated on the inside surface of the catalyst zone.

In order to get a sufficient amount of void space to have proper gas movement through a packed catalyst zone, it is preferred that the catalyst particles have a diameter from about 1% to about 20% of the diameter of the catalyst zone, or more preferably approximately 10% of the diameter of the catalyst zone. However, larger or smaller particles may be used in some circumstances.

The only requirements for the catalyst is that it must have a sufficiently low vapor pressure to survive in the vacuum in the enclosure, and that it can either be formed into particles of the correct size or coated onto such particles or coated on the inside surface of the reactor. The catalyst may be supported or unsupported, a solid, or even a liquid, if its vapor pressure is sufficiently low and if it can be coated onto an inert support, or the surface of the catalyst zone.

While the gas is moving through the catalyst zone, under the conditions outlined above, it has been estimated that, on the average, a given molecule of gas will collide with the surface of the catalyst from about 100 to about $10^6$ times and possibly more times for catalysts that are microporous solids, and will collide with other gas molecules about $10^3$ a times, or less. If the catalyst is coated on the inside surface of the catalyst zone, the number of collisions with the catalyst will be near the low end of the range, if the catalyst zone is packed, the number of collisions with the catalyst will be somewhat higher in the range. A packed catalyst zone is preferred.

The number of collisions experienced can be controlled within these ranges, for instance by controlling the number of molecules of reactant gas in the pulse, by using larger or smaller particles of catalyst to change the amount of void space in the catalyst zone, by lengthening or shortening the length of the catalyst zone, by increasing or decreasing the diameter of the catalyst zone, or by other techniques. In this way, the amount of reaction can be controlled, so that sufficient intermediates and products are produced so they can be detected, and yet the amount of reaction is limited so that at least some of the fragile and highly reactive intermediates remain unreacted. The amount of reaction can also be controlled to some extent by controlling other parameters, such as temperature, duration of the pulse, etc.

As a result of this flexibility the number of collisions can be controlled so that a large enough number of collisions occur so that TAP can be used with a large number of commercially important catalysts and catalyzed reactions. At the same time, the number of collisions of the fragile and reactive intermediates can be limited so that a significant portion of them survive and can be detected and analyzed.

The reactor also has an outlet means, through which the product gas mixture that has moved through the catalyst and reacted, can exit. As used here, "product gas" or "product pulse" is considered to be the gas mixture made up of reactants, intermediates, and products that has moved through the catalyst zone. The product gas exits as a pulse. However, the product gas pulse is of substantially longer duration than the very rapid pulse of reactant gas.

The gas molecules will leave the outlet means via molecular flow, that is by traveling through the substantial vacuum of the enclosure with the same trajectories that the molecules have as they diffuse out of the catalyst zone. It is preferred that the outlet means not unduly interfere with this molecular flow. The outlet means should, preferably have a restraining device to hold the catalyst in the catalyst zone, in similar fashion to the inlet means. A screen is preferred, with a stainless steel screen more preferred.

A portion of the molecularly flowing product pulse will be moving directly toward the detector, with other portions moving obliquely. The TAPRS has at least one aperature situated directly between the outlet means of the reactor and the detector, and preferably two or more collimated aperatures. The aperature can either be fixed or adjustable. This aperature serves to block any molecules not moving in a substantially straight path from the reactor to the detector. In this way the aperature serves to resolve the pulse of product gas into a pulse in which the molecules are moving in substantially parallel paths toward the detector. The preferred type of aperature is a slit or an iris, more preferably an adjustable slit or iris.

Resolution of the product gas pulse is important because the distribution curve of molecules of various types as they are distributed in time within a pulse is important information. If molecules can reach the detector through a circuitous route ricocheting off the walls of the enclosure, this distribution in time within the pulse could be masked.

The resolved product pulse then moves to the detection and analysis--portion of TAPRS. It is important that the detection and analysis be done in real time. As used herein, the phrase "real time analysis" means that the detection and analysis occur while the pulse is in the enclosure. Delayed methods of analysis such as collecting samples for later analysis or chromatographic techniques, would not allow for analysis of the distribution curve of molecules in time within a pulse, and would also allow for further reaction of the fragile and reactive intermediates.

Examples of real time analyses include mass spectrometry and laser induced fluorescence, time resolved infrared or ultraviolet/visible light spectroscopy, and the like, with mass spectrometry being preferred, and with mass spectrometry using a quadrupole mass analyzer, because it is compact and can easily be adapted to and fitted into the enclosure. The size and design of the quadrupole mass analyzer can be varied, in a manner known to one skilled in the art, depending upon the sensitivity and mass range desired. Because a quadrupole mass spectrometer is the preferred type of detector, the remainder of the discussion will focus on that type of detector. Similar considerations to other types of detection and analysis systems.

The ionization mechanism can be any suitable ionization known in mass spectrometry, with photoionization and electron impact ionization being preferred. However, it is preferred that fragmentation of molecules during ionization be minimized. The quadrupole can be oriented parallel to or perpendicular to the flow of the resolved product pulse. It is only required that the ionization chamber be in a substantially straight line with the reactor outlet and the aperature so that it is in the path of flow of the resolved product pulse. It is preferred that the quadrupole be perpendicular to the flow of the resolved product pulse, to avoid having unionized species striking the detector.

The mass analyzer operates most efficiently at pressures below about $10^{-6}$ torr and more preferably below about $10^{-8}$ torr. Because of the presence of the catalyst with a very large surface area and because of injection of the reactant gas and other gases and because of product gas rebounding from the area surrounding the aperature, it is difficult to reduce the pressure near the reactor to this low a level. For this reason, it is preferred that the sector surrounding the reactor and the sector surrounding the detector have separate vacuum systems to produce a differentially pumped high vacuum system. The aperature or slit is a convenient divider for separating the two vacuum sectors. If two collimated aperatures or slits are used, the enclosure can be divided into three vacuum sectors, etc. The larger the number of vacuum sectors, the greater the differential in vacuum that can be attained between the reactor sector and the detector sector. It is also preferred that there be a means, such as a valve, for closing off the reactor sector from the remainder of the enclosure, so the reactor can be changed or serviced without breaking vacuum in the remainder of the enclosure.

The mass analyzer will normally scan the intensity variation of the specified mass within a particular pulse as a function of time. Various masses can be similarly analyzed to produce a complete profile of reaction products and intermediates for each pulse.

The action of the analysis means must be coordinated with the pulsing mechanism, so that the time periods over which the analysis means is scanning coincide with the arrival of a resolved pulse of product gas. This can be accomplished by a conventional electronic timing mechanism, known to one skilled in the art. A timing mechanism can either be set up to trigger both the pulsing mechanism and the analysis means or it can be set up to sense the action of the pulsing means and trigger the analysis means in response.

The signal from the mass analyzer can be processed by conventional electronic means. It is preferred that the results of several scans be averaged to arrive at composite results. This averaging will account for statistical variations that may occur among different pulses.

The masses which are observed by the mass analyzer indicate reactants and the products and intermediates produced in the catalyzed reaction. And, the intensity variation curve for each mass scanned, and how these curves compare with the theoretical distribution curves, or with curves of other masses, gives an indication of the sequence and timing with which the molecules or fragments were produced in the catalyzed reaction.

The sequence and timing of production of the intermediates and products gives information relating to such things as mechanisms and kinetics of the catalyzed reaction. Changes in the distribution curve that occur as temperature changes can give indications of a number of things, such as how mechanisms and catalyst activity change with temperature, and of the desorption activation energy. TAP is also quite sensitive to the effects of changes in surface conditions of the catalyst. Other conclusions that can be drawn from this type of data would be known to one skilled in the art.

DESCRIPTION OF THE DRAWINGS

FIG. 1 represents a typical TAPRS, with an enclosure (1), containing a reactor (2), and a high speed valve (3), to create the very rapid pulse of reactant gas, with a feed line for the reactant gas (4). The valve is connected to a mixing zone (5) contained in a transition piece located between the valve and the reactor. The transition piece is also fitted with a feed line for continuous feed (6), which may be used if desired. A product pulse (7) leaves the reactor and passes through an opening in a cryogenic plate (8), and passes through two collimated, adjustable slits (9), to produce a resolved product pulse (10). The resolved product pulse enters the ionization chamber (11) of a quadrupole mass analyzer (12). The quadrupole mass analyzer scans the resolved product pulse for the mass designated in the mass spectrometer electronics (13). The signal from the quadrupole mass analyzer is processed in usual fashion by the mass spectrometer electronics, and is sent to the signal averager (14). The signal averager is regulated by a clock (15), connected to a pulse generator (16) that activates the valve causing injection of a pulse of reactant gas. The clock senses a pulse and activates the signal averager to receive a signal for a designated period of time and to store it. Normally the signal averager stores the signals from a series of pulses and averages them to reduce noise. The averaged signal is fed to a computer (17). The computer can be used to simply run a plotter (18) to plot the results, or the computer can store the signal and compile signals for each of the masses studied, to plot them all together or the computer could be used to calculate things such as the time of the intensity peak for a particular mass, the median residence time, a time weighted median residence time, or other values based upon the curves. In this configuration, the enclosure is divided into three sectors, the reactor sector (19), an intermediate sector (20), and the analyzer sector (21), each of which is equipped with its own vacuum pump (22). Additionally, the intermediate sector has a liquid nitrogen trap (23) to assist in maintaining vacuum. This multiple sector arrangement is useful to allow the mass analyzer to operate in a higher vacuum than it is possible to attain in the reactor sector.

EXAMPLES

Figure 1:
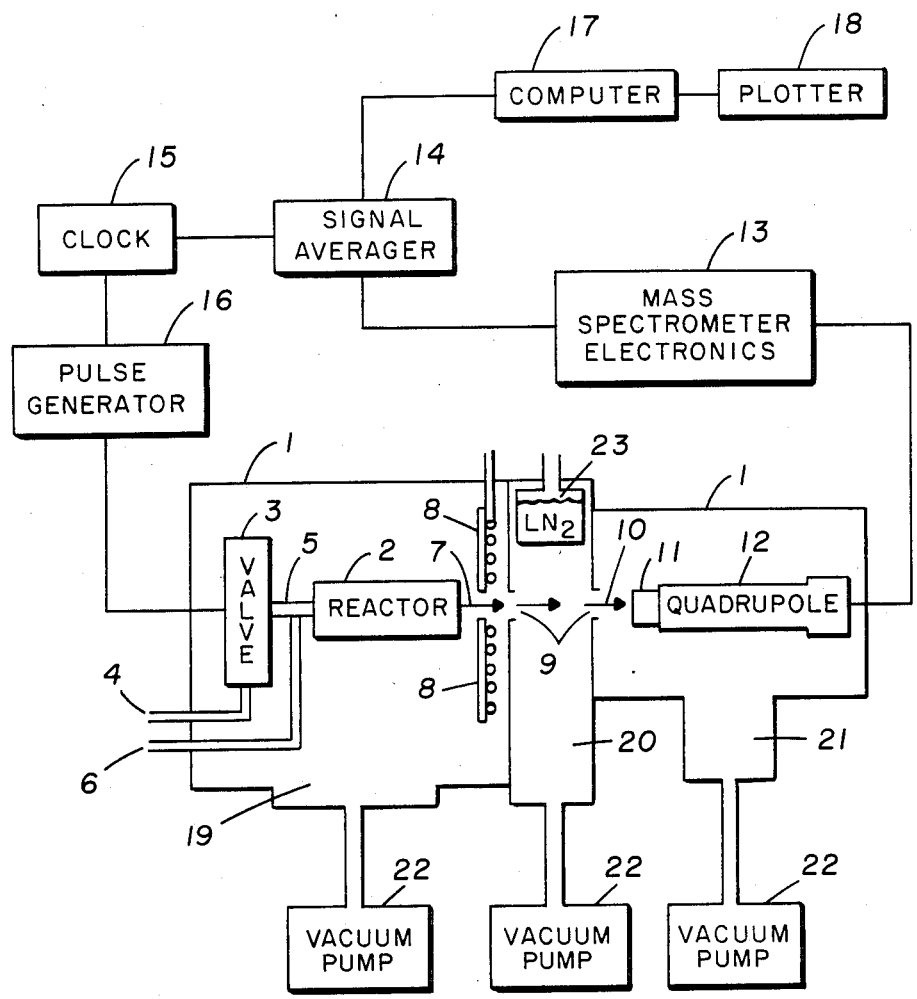
FIG. 1 is a schematic representation of a TAPRS.

In the Examples, the following procedure was used, with a TAPRS similar to the schematic in FIG. 1.

A sample of the catalyst was prepared and sized to 500±50 microns, and charged to the reactor with a catalyst zone about 0.635 cm in diameter and about 1.27 cm in length. The reactor was placed in the enclosure, which was evacuated.

A blend of reactants was prepared and was fed to a high speed pulse valve. The valve was set to introduce a pulse with an average duration, measured at full width, half maximum of about 200 microseconds. The pressure of the feed gas was adjusted so that approximately $10^{15}$ molecules entered the reactor with each pulse.

The intensity variation of the indicated mass within a particular pulse was scanned as a function of time.

Three time points could be calculated as appropriate for the type of experiment being conducted.

One is simply the time of maximum intensity, also called the time of peak maximum (TPM).

The second is the median residence time (MRT), which is the time at which 50% of the molecules of interest within a particular pulse have exited the reactor. Since the area under the curve, for a plot of mass intensity versus time, is directly related the number of molecules that have exited the reactor, the MRT is the time at which 50% of the curve area is realized, or the time at which the area under the curve to that point is equal to $$\tfrac{1}{2}\int_0^\infty I(t)dt,$$

where I(t) is the observed mass intensity as a function of time.

The third is the average residence time or the time-weighted residence time, $<tr>$, which is most conveniently obtained directly from the mass intensity curve by evaluating the following expression:

$$<tr> = \frac{\int_0^\infty tI(t)dt}{\int_0^\infty I(t)dt}$$

where t is time and I(t) is the observed mass intensity as a function of time.

EXAMPLE 1

A catalyst of the composition $V_1P_{1.050}O_x$ was prepared according to the procedure of Example 1 of U.S. Pat. No. 3,907,707, which is incorporated herein by reference. A 0.5 g sample of the catalyst was charged to the reactor. The reactor was placed in the TAPRS and the enclosure was evacuated. The temperature of the reactor was maintained at about 500° C.

The reactant gas was a blend of about 30 mole % butane and about 70 mole % oxygen with an absolute pressure of about 120 torr. The mixture was pulsed into the reactor.

The analysis of the resolved product pulse indicated masses at 54, 56, and 68, which correspond to butadiene, butene, and furan. The TMP's were as follows: butane, 8.5 milliseconds; butene, 10.5 milliseconds; butadiene, 14.5 milliseconds; and furan, 22 milliseconds.

Since this catalyst converts this feed gas into maleic anhydride, the data above indicate that butene, butadiene, and furan are all intermediates in that reaction. The various TPM's indicate that the reaction sequence is as follows:

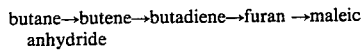

butane→butene→butadiene→furan →maleic anhydride

Figure 2:
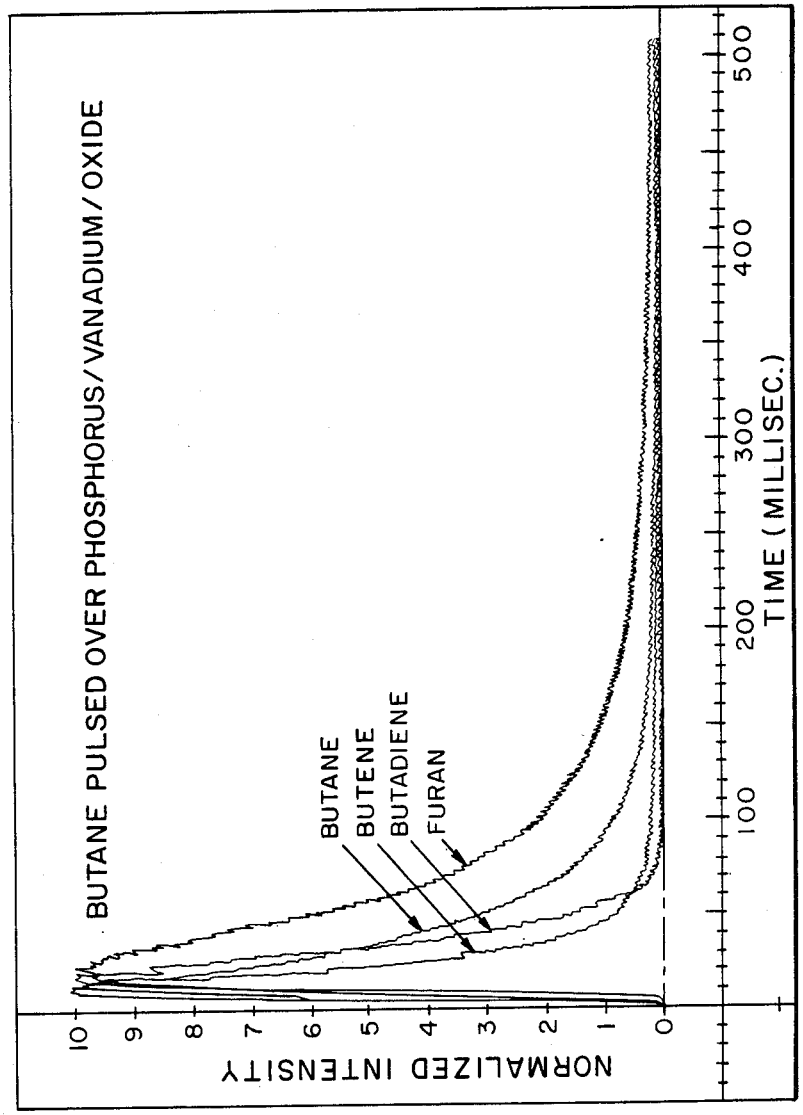
FIGS. 2-5 are examples of data obtained from TAP experiments and will be discussed with the Examples.

The plots of the normalized intensity curves for butane, butene, butadiene, and furan are shown in FIG. 2.

EXAMPLE 2

A catalyst of the following composition, $Mn_{1.25}PO_x$-50 wt. % $SiO_2$ was prepared according to the procedure of Example 1 of U.S. Pat. No. 4,457,905, which is incorporated herein by reference. In a conventional fluid bed reactor, at 450° C., a mixture of 7.2% $NH_3$, 7.0% $CH_3OH$, 18% $O_2$, and the balance inert, produces HCN in 88% yield.

A 0.45 g sample of the catalyst was placed in the reactor, which was placed into the TAPRS as above. The reactor was maintained at 450° C.

A reactant gas blend was prepared of about 28.6 mole % each of methanol, ammonia, and oxygen and about 14.3% argon with an absolute pressure of about 245 torr. This mixture was pulsed into the reactor.

Figure 3:
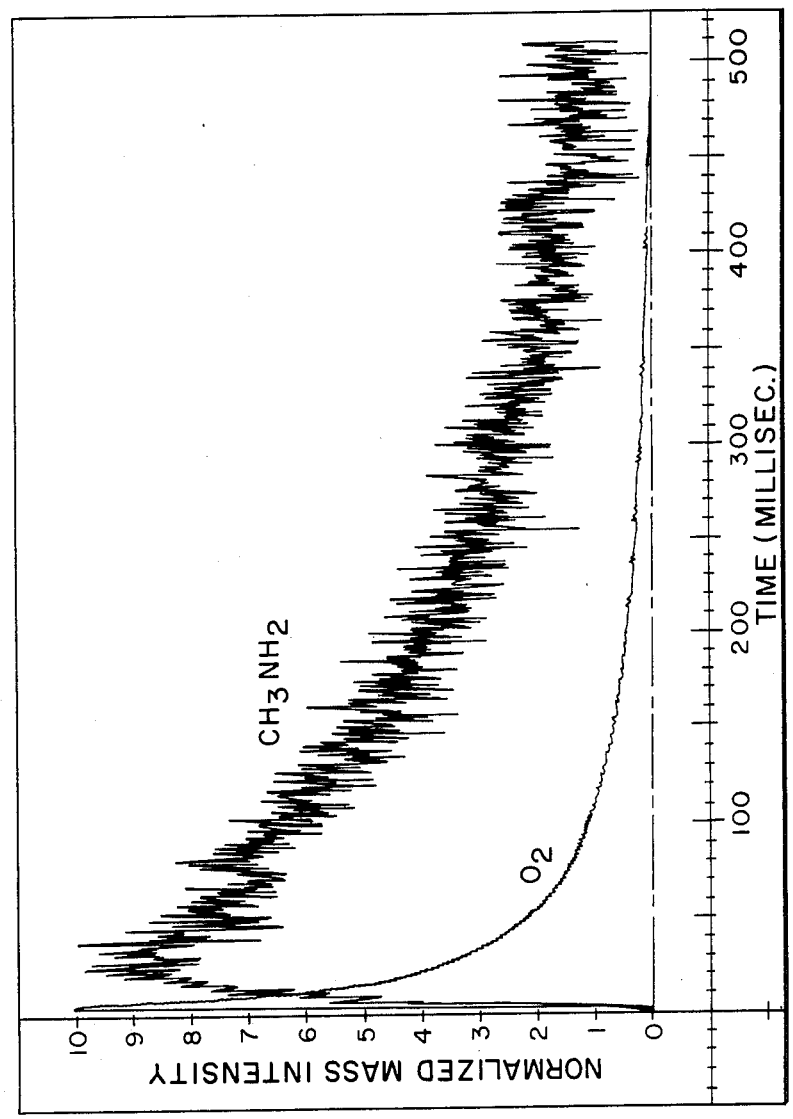

Analysis of the product gas indicated formation of methylamine, mass 30, but no measurable HCN, mass 26, was formed. FIG. 3, which shows the curves for oxygen and methylamine, helps to explain the lack of HCN formation. When the intensity curve for methyl amine is at its peak, about 40 milliseconds, the intensity curve for oxygen is far past its peak, so that oxygen is not present in the reactor in sufficient quantities for further reaction of the methyl amine. This could be solved by either pulsing oxygen somewhat later than the remainder of the gas mixture, or by feeding oxygen on a continuous basis.

Another set of runs was performed in which molecular oxygen was fed continuously during pulsing, and hydrogen cyanide and water were produced as expected.

This Example demonstrated that methyl amine is an intermediate in the reaction and that oxygen is required for the methyl amine to complete the reaction.

EXAMPLE 3

A sample 0.5 g of $Bi_2MoO_6$, gamma bismuth molybdate, as commercially available, was placed into the TAPRS. Gamma bismuth molybdate is known to catalyze the formation of acrolein from propylene and oxygen.

Knowledge of the desorption energy of the acrolein is important for assessing selectivity losses after product formation. TAP can be used to determine the desorption energy, $E_d$.

At constant temperature, in a TAP experiment, the time-weighted residence time $<tr>$ is related to the rate of desorption, $k_d$, by the following expression:

$$<tr> = Cl\,[1+(k_a/k_d)]$$

where $k_a$ is the rate of adsorption and C is a constant dependant upon configuration of the catalyst.

From this it can be shown that a plot of $\ln[<tr>-<tr>']$ where $<tr>$ is the time-weighted residence time of acrolein, and $<tr>'$ is the time-weighted residence time of an inert gas, such as argon, versus $1/T$, where T is temperature in degrees Kelvin gives a straight line with a slope of $E_d/k$, where k is Boltzmann's constant from the Arrhenius expression. Thus $E_d$, the desorption energy, can be determined.

Figure 4:
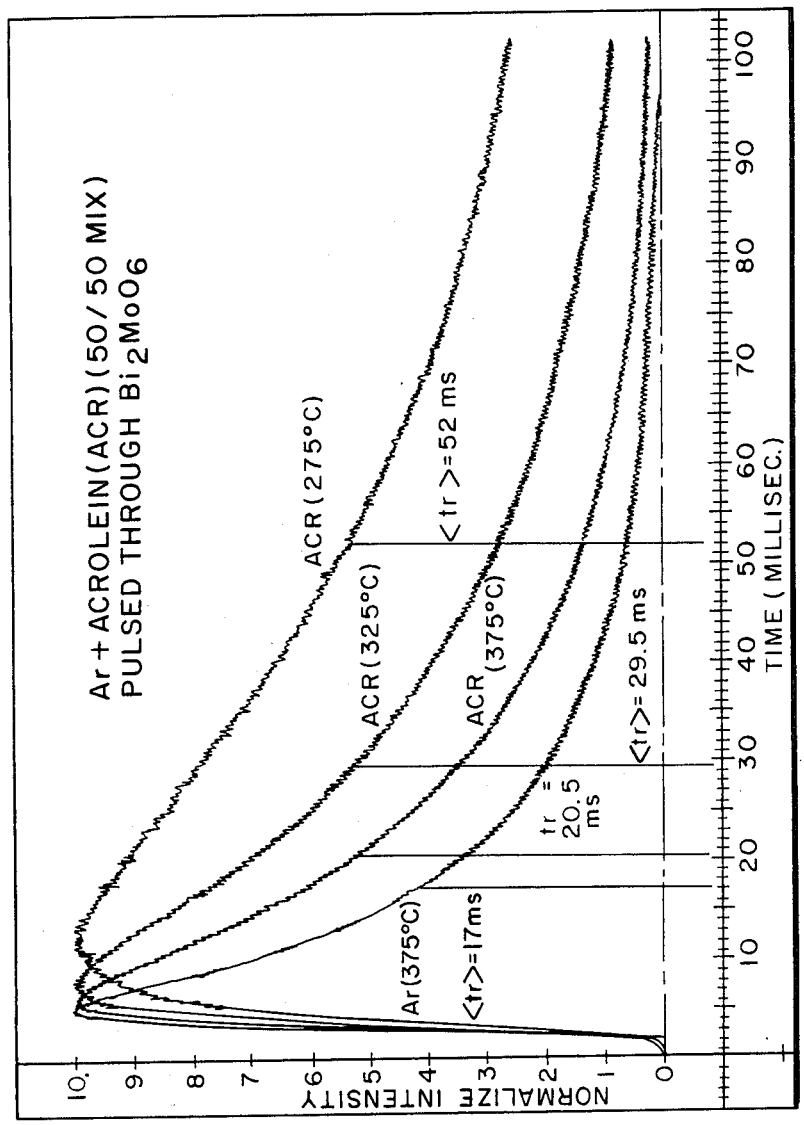

A blend containing about 50 mole % each of acrolein and argon with an absolute pressure of about 50 torr was pulsed into the reactor containing the gamma bismuth molybdate over varying temperatures. Examples of some of the curves obtained, with labeled $<tr>$ times are shown in FIG. 4.

Figure 5:
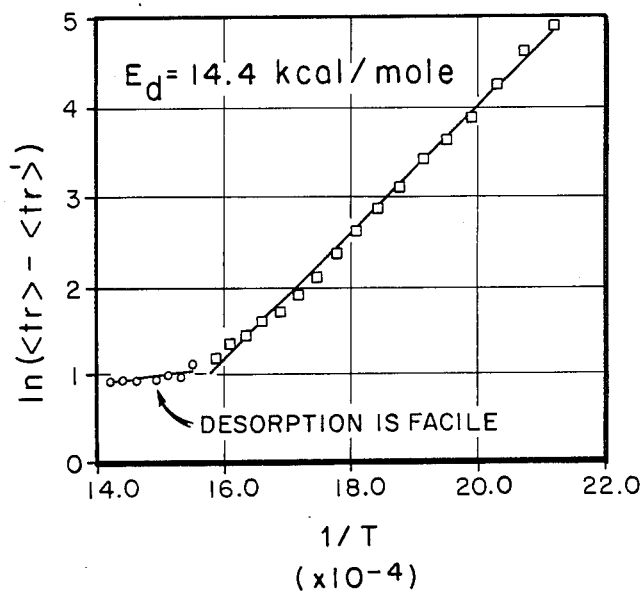

Analysis of all of the data gives a plot shown in FIG. 5. Below about 625° K., the desorption energy is about 14.4 kcal/mole. Above about 625° K., desorption becomes facile, and we can infer that the surface has changed. Importantly, the best catalytic activity is best above about 625° K.

These Examples, and the Figures, are intended as illustrative only, and are not in any way intended to limit the scope of this invention. One skilled in the art will recognize many alterations and changes that can be made from the above, without deviating from the spirit and scope of this invention.

We claim:
1. An apparatus comprising:
   (a) an enclosed housing and means for producing a vacuum within the housing;
   (b) within said housing, a reactor having a zone defined in the reactor containing a packed particulate reaction catalyst, said reactor being structured to allow a reactant gas to pass through the packed particles of the catalyst to produce a product gas by a slow reaction;
   (c) means for introducing a rapid pulse of said reactant gas to said reactor and means for controling conditions such that a given molecule of said gas will collide with the surfaces of said catalyst from about 100 to $10^6$ times and with other gas molecules about $10^3$ or less;
   (d) means for withdrawing from said reactor a pulse of product gas;
   (e) within said housing, means for resolving said pulse of product gas to produce a resolved pulse of product gas in which molecules of product gas move in substantially parallel paths;
   (f) means for providing real time analysis of said resolve pulse of product gas; and
   (g) means for coordinating the actions of said rapid pulse introducing means and said analysis means so that scanning by said analysis means coincides with the arrival of a resolved pulse of product gas.

* * * * *

UNITED STATES PATENT AND TRADEMARK OFFICE
CERTIFICATE OF CORRECTION

PATENT NO. : 4,626,412

DATED : December 2, 1986

INVENTOR(S) : Jerry R. Ebner, et al.

It is certified that error appears in the above—identified patent and that said Letters Patent is hereby corrected as shown below:

Column 2, line 27, "moleoule" should read -- molecule --.
Column 2, line 27, "moleoules" should read -- molecules --.
Column 2, line 28, "$10^S$" should read -- $10^6$ --. Column 4, line 52, "$10^{-6}$ torr" should read -- $10^{-6}$ torr. --.
Column 5, line 42, "$10^3$ a times" should read -- $10^3$ times --. Column 6, line 44, "analysis--portion" should read -- analysis portion --. Column 9, line 41, "$V_1P_{1.050}O_x$" should read -- $V_1P_{1.05}O_x$ --.
Column 10, line 51, "Cl[1+" should read -- C[1+ --. Column 11, line 19, "the reactor" should read -- the "reactor --.
Column 11, line 20, "reaction" should read -- reaction" --.

Signed and Sealed this

Twenty-second Day of September, 1987

Attest:

DONALD J. QUIGG

Attesting Officer     Commissioner of Patents and Trademarks